US00PP37474P3

(12) United States Plant Patent
Schoone

(10) Patent No.: US PP37,474 P3
(45) Date of Patent: Jun. 16, 2026

(54) ***PHALAENOPSIS* PLANT NAMED 'Pont Neuf'**

(50) Latin Name: *Phalaenopsis hybrida*
Varietal Denomination: Pont Neuf

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/354,780

(22) Filed: Oct. 9, 2025

(65) Prior Publication Data

US 2026/0123560 P1 Apr. 30, 2026

Related U.S. Application Data

(60) Provisional application No. 63/714,593, filed on Oct. 31, 2024.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

(56) References Cited

U.S. PATENT DOCUMENTS

PP33,857 P2 * 1/2022 Schoone ..... A01H 6/62
Plt./311

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'Pont Neuf', characterized by its upright plant habit; moderately vigorous growth habit; strong flowering stems; healthy and sturdy leaves; freely flowering habit with typically two inflorescences developing per plant, each inflorescence with numerous flowers; flower petals and sepals that are reddish purple in color and darker reddish purple-colored labella; and good postproduction longevity.

2 Drawing Sheets

Figure 1:
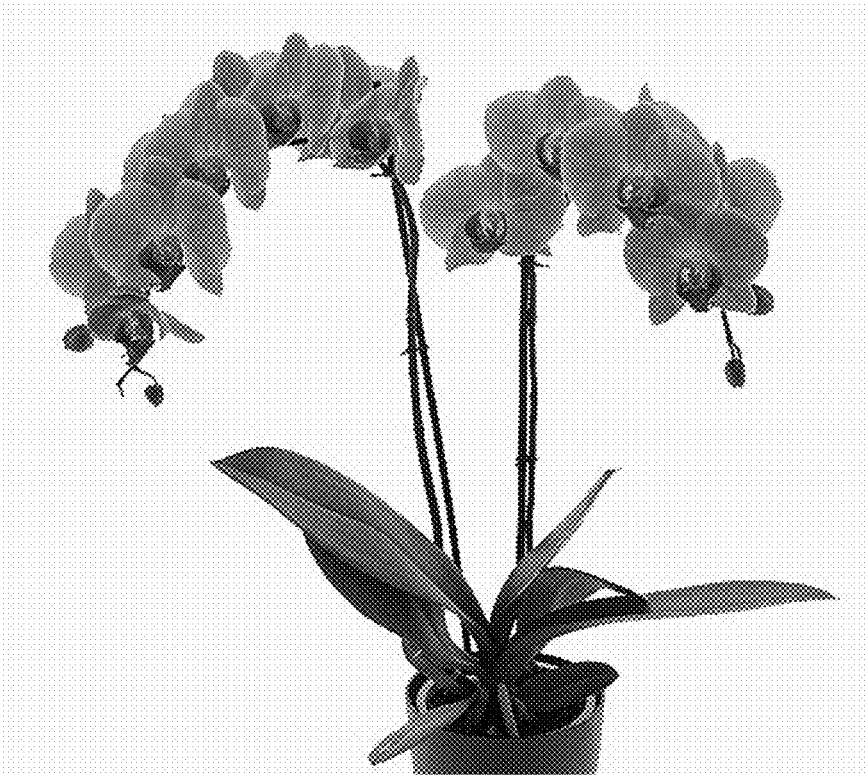

Botanical designation: *Phalaenopsis hybrida.*
Cultivar denomination: 'PONT NEUF'.

CROSS-REFERENCED TO CLOSELY-RELATED APPLICATIONS

A European Community Plant Breeder's Rights application for the instant plant was filed by the Applicant/Assignee, Floricultura B.V. of Heemskerk, The Netherlands on Dec. 4, 2024, application number 2024/3017. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Pont Neuf'.

The new *Phalaenopsis* plant is a product of a planned breeding program conducted by the Inventor in De Lier, Heemskerk and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in July, 2014 in De Lier, The Netherlands of a proprietary selection of *Phalaenopsis hybrida* identified as code number ST3710, not patented, as the female, or seed, parent with a proprietary selection of *Phalaenopsis hybrida* identified as code number B3181, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November, 2020.

Asexual reproduction of the new *Phalaenopsis* plant by in vitro meristem propagation in a controlled environment in Assendelft, The Netherlands since December, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Pont Neuf'. These characteristics in combination distinguish 'Pont Neuf' as a new and distinct *Phalaenopsis* plant:

1. Upright plant habit.
2. Moderately vigorous growth habit.
3. Strong flowering stems.

4. Healthy and sturdy leaves.
5. Freely flowering habit with typically two inflorescences developing per plant, each inflorescence with numerous flowers.
6. Flower petals and sepals that are reddish purple in color and darker reddish purple-colored labella.
7. Good postproduction longevity.

Plants of the new *Phalaenopsis* can be compared to plants of the female parent selection. Plants of the new *Phalaenopsis* differ primarily from plants of the female parent selection in the following characteristics:

1. The lateral lobes of the labella of plants of the new *Phalaenopsis* are mostly purplish red in color whereas the lateral lobes of the labella of plants of the female parent selection are mostly white in color.
2. The central lobe of the labella of plants of the new *Phalaenopsis* are mostly purplish red in color whereas the central lobe of the labella of plants of the female parent selection are mostly white in color.

Plants of the new *Phalaenopsis* can be compared to plants of the male parent selection. Plants of the new *Phalaenopsis* differ primarily from plants of the male parent selection in the following characteristics:

1. Flower petals of plants of the new *Phalaenopsis* are reddish purple in color whereas flower petals of plants of the male parent selection are white in color.
2. Flower petal venation of plants of the new *Phalaenopsis* is more conspicuous than flower petal venation of plants of the male parent selection.

Plants of the new *Phalaenopsis* can be compared to plants of x *Phalaenopsis hybrida* 'Precious Love', disclosed in U.S. Plant Pat. No. 33,857. In side-by-side comparisons, plants of the new *Phalaenopsis* differ primarily from plants of 'Precious Love' in the following characteristics:

1. Leaves of plants of the new *Phalaenopsis* are longer than leaves of plants of 'Precious Love'.
2. Flower petal venation of plants of the new *Phalaenopsis* is less conspicuous than flower petal venation of plants of 'Precious Love'.
3. Flowers of plants of the new *Phalaenopsis* have white-colored centers whereas flowers of plants of 'Precious Love' do not have white-colored centers.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Pont Neuf' grown in a container.

Figure 2:
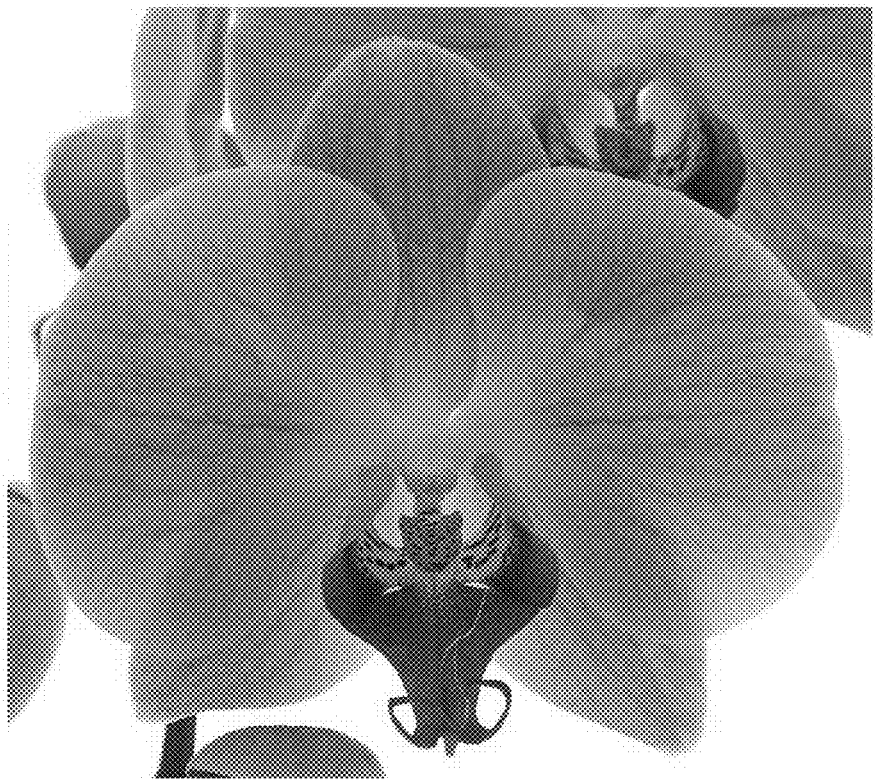

The photograph on the second sheet (FIG. 2) is a close-up view of a typical flower of 'Pont Neuf'.

DETAILED BOTANICAL DESCRIPTION

The aforementioned photographs and following observations and measurements describe plants grown during the winter in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Pont Neuf'.

Parentage:

*Female, or seed, parent*.—Proprietary selection of *Phalaenopsis hybrida* identified as code number ST3710, not patented.

*Male, or pollen, parent*.—Proprietary selection of *Phalaenopsis hybrida* identified as code number B3181, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous and moderate growth rate.

*Plant height, substrate level to top of foliar plane*.—About 20.1 cm.

*Plant height, substrate level to top of floral plane*.—About 43.1 cm.

*Plant diameter or spread*.—About 38 cm.

Leaf description:

*Arrangement and quantity*.—Distichous, simple; sessile; about four to six fully-developed leaves per plant.

*Length*.—About 21.5 cm.

*Width*.—About 7.3 cm.

*Aspect*.—Semi-erect.

*Shape*.—Narrowly obovate to narrowly elliptic; slightly carinate.

*Apex*.—Unequal narrowly obtuse.

*Base*.—Sheathing. Sheath length: About 1.7 cm. Sheath width: About 1.3 cm. Sheath color, upper and lower surfaces: Close to 146C, apical margins, tinged with close to N186C.

*Margin*.—Entire.

*Texture and luster, upper surface*.—Smooth, glabrous; slightly glossy.

*Texture and luster, lower surface*.—Smooth, glabrous; moderately glossy.

*Venation pattern*.—Camptodromous.

*Color*.—Developing leaves, upper surface: Close to NN137A; narrow marginal edges, close to N186C. Developing leaves, lower surface: Close to 146A strongly tinged with close to N186C. Fully expanded leaves, upper surface: Close to a blend of NN137B and 146A; narrow marginal edges, close to 152A; venation, close to a blend of NN137A and 146A. Fully expanded leaves, lower surface: Close to 146B moderately to strongly tinged with close to N186C; venation, close to 137A, distally, close to N186C.

Inflorescence description:

*Appearance and flowering habit*.—Showy zygomorphic flowers arranged on axillary simple or branched racemes; typically two inflorescences develop per plant; each inflorescence with about eleven flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about 14 weeks on the plant; flowers not persistent.

*Inflorescence length* (*lowermost flower to inflorescence apex*).—About 27.4 cm.

*Inflorescence width*.—About 14.9 cm.

*Flower buds* (*about one week before flower opening*).—Height: About 1.9 cm. Diameter: About 1.4 cm. Shape: Broadly ovoid. Color: Close to N77B; towards the apex and base, close to N186D.

*Flower size*.—About 8.4 cm (vertical) by 9.4 cm (horizontal).

*Flower depth*.—About 3.4 cm.

*Petals, quantity and arrangement*.—Three, two lateral petals and one center petal transformed into a labellum.

*Lateral petals*.—Length: About 4.5 cm. Width: About 6 cm. Shape: Broadly reniform to close to broadly lunate; not imbricate. Apex: Obtuse. Margin: Entire. Texture and luster, upper and lower surfaces: Smooth, glabrous; moderately velvety; matte. Color: When opening, upper surface: Close to a blend of NN78D and N80B; towards the margins, close to 76C; towards the base, close to 76D; venation, close to a blend of N78B and NN78B. When opening, lower surface: Close to a blend of N75A and N78D; towards the margins, close to 76C; venation, close to a blend of N78B and NN78B. Fully opened, upper surface: Close to a blend of N78C and NN78D; towards the apex and margins, close to a blend of 77C and N78D; towards the base, close to 75D; venation, close to N78B; colors do not change with subsequent development. Fully opened, lower surface: Close to N75C; narrow marginal edges, close to 76C; venation, close to N78B and N78C; colors do not change with subsequent development.

*Labella*.—Appearance: Three-parted with two lateral lobes and a central lobe. Length, lateral lobes: About 2.4 cm. Width, lateral lobes: About 1.7 cm. Length, central lobe: About 2.4 cm. Width, central lobe: About 0.8 cm to 2.5 cm. Length, cirrhose apices: About 2.8 cm. Shape, lateral lobes: Obovate. Shape, central lobe: Deltoid. Apex, lateral lobes: Obtuse. Apex, central lobe: Acute with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 5.5 mm in length, about 7 mm in width and about 6.5 mm in height. Color, lateral lobes: When opening and fully opened, upper surface: Close to 183B; towards the apex, close to N80B; at the base, close to NN155A and NN155B with stripes and blotches, close to 183B. When opening and fully opened, lower surface: Close to N80B; towards the base, close to 159C and at the base, close to 183C. Color, central lobe: When opening and fully opened, upper surface: Close to 184A; towards the apex, close to 71C with apex, close to NN78D; at the base, close to 155A with radial stripes, close to 183B; cirrhose apices, close to 71C, distally, close to 11B. When opening and fully opened, lower surface: Close to N78B and 183C; at the base, close to 160C; main vein, close to 182C; cirrhose apices, close to N78B, distally, close to 11B. Color, callosities: When developing: Close to 13C densely covered with dots and blotches, close to 184A. Fully developed: Close to 11B densely covered with dots and blotches, close to 183B.

*Sepals*.—Quantity and arrangement: Three, one upper dorsal sepal and two lower lateral sepals. Length, dorsal sepal: About 4.6 cm. Width, dorsal sepal: About 3.4 cm. Length, lateral sepals: About 4.7 cm. Width, lateral sepals: About 3.2 cm. Shape, dorsal sepal: Broadly elliptic to broadly elliptic- obovate. Shape, lateral sepals: Ovate. Apex, dorsal sepal: Minutely retuse. Apex, lateral sepals: Bluntly acute. Base, dorsal and lateral sepals: Cuneate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to N78C; towards the margins, close to 76C; at the base, close to 76B; venation, close to a blend of N78B and NN78B. When opening, lower surface: Close to 72B; towards the apex and margins, close to N78C; narrow marginal edges, close to 76C. Fully opened, upper surface: Close to a blend of N78C and NN78D; towards the apex and margins, close to a blend of 77C and N78D; narrow marginal edges, close to 76C; at the base, close to 75D; venation, close to N78B. Fully opened, lower surface: Close to a blend of N78B and NN78C; towards the apex and margins, close to N78C; narrow marginal edges, close to 76C. Color, lateral sepals: When opening, upper surface: Close to N78D; towards the margins, close to 76C; at the base, close to 160D with fine dots, close to N79C. When opening, lower surface: Close to N78D; at the base, close to 160D; venation, close to 71B. Fully opened, upper surface: Close to N78C; narrow marginal edges, close to 76C; at the base, close to 160C and 160D with fine dots, close to NN78A. Fully opened, lower surface: Close to NN74B; towards the apex and margins, close to N78C; at the base, close to 160C and 160D; venation, close to NN74A and NN74B.

*Peduncles*.—Length: About 53.9 cm. Diameter: About 5 mm. Strength: Strong. Aspect: Upright to outwardly arching. Texture and luster: Smooth, glabrous; matte. Color: Close to a blend of 147A and 200A; moderately covered with fine dots and fine marbling, close to 147B.

*Pedicels*.—Length: About 3.9 cm. Diameter: About 3 mm. Strength: Moderately strong. Aspect: About 50° from peduncle axis. Texture and luster: Smooth, glabrous; matte. Color: Close to 195B; distal end, close to 159C; proximal end, close to 176B.

*Reproductive organs*.—Androecium: Column length: About 9 mm. Column width: About 6 mm. Column color: Close to 76B. Pollinia quantity: Two. Pollinia diameter (per two pollinia): About 2.5 mm. Pollinia color: Close to 23A. Gynoecium: Stigma length: About 4 mm. Stigma width: About 5 mm. Stigma shape: Reniform. Stigma color: Close to N155A. Ovary length: About 1 cm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Pont Neuf' as herein illustrated and described.

* * * * *